United States Patent
Wang

(10) Patent No.: US 9,687,570 B2
(45) Date of Patent: Jun. 27, 2017

(54) METHOD AND DEVICE FOR PRODUCING OPTIMIZED LIPID-BASED MICRO/NANO-BUBBLES

(71) Applicant: Trust Bio-sonics Inc., Hsinchu (TW)

(72) Inventor: Chung-Hsin Wang, Hsinchu (TW)

(73) Assignee: Trust Bio-Sonic Inc., HsinChu (TW)

( * ) Notice: Subject to any disclaimer, the term of this patent is extended or adjusted under 35 U.S.C. 154(b) by 275 days.

(21) Appl. No.: 14/248,338

(22) Filed: Apr. 9, 2014

(65) Prior Publication Data

US 2014/0328767 A1 Nov. 6, 2014

(30) Foreign Application Priority Data

May 3, 2013 (TW) .............................. 102115967 A

(51) Int. Cl.
| | | |
|---|---|---|
| A61K 8/00 | (2006.01) | |
| A61K 49/22 | (2006.01) | |
| A61K 41/00 | (2006.01) | |
| B01F 3/04 | (2006.01) | |
| B01F 11/02 | (2006.01) | |
| B01F 15/06 | (2006.01) | |

(52) U.S. Cl.
CPC ........ A61K 49/223 (2013.01); A61K 41/0028 (2013.01); B01F 3/04099 (2013.01); B01F 11/0266 (2013.01); B01F 15/06 (2013.01); A61K 49/22 (2013.01); B01F 2015/062 (2013.01); B01F 2215/0034 (2013.01); B01F 2215/0404 (2013.01)

(58) Field of Classification Search
None
See application file for complete search history.

(56) References Cited

U.S. PATENT DOCUMENTS

| | | | |
|---|---|---|---|
| 5,874,062 A * | 2/1999 | Unger ................ | A61K 49/1806 424/450 |
| 5,922,304 A | 7/1999 | Unger | |
| 2012/0175305 A1 | 7/2012 | Borden et al. | |

FOREIGN PATENT DOCUMENTS

| | | |
|---|---|---|
| CN | 101528268 A | 9/2009 |
| CN | 102552947 A | 7/2012 |
| WO | WO2009059449 A1 | 5/2009 |

OTHER PUBLICATIONS

Transparency and translucency Wikipedia 2017.*
Feshitan et al., "Engineering Lipid-Stablized Microbubbles for Magnetic Resonance Imaging Guided Focused Untrasound Surgery", Academic Commons—Columbia University, 2012, XP002734009, Retrieved from internet: URL:http://academiccommons.columbia.edu/catalog/ac:175647.
Controlling the Size Distribution of Lipid-Coated Bubbles Via Fluidity Regulation from Ultrasound in Med. & Biol., vol. 39, No. 5, pp. 882-892, 2013.
Surface phase behavior and microstructure of lipid/PEG-emulsifier monolayer-coated microbubbles by Mark A. Borden et al. from Colloids and Surfaces B: Biointerfaces 35 (2004) 209-223.
The Effect of Preactivation Vial Temperature on the Acousti Properties of Definitytm by Brandon L. Helfield et al from Ultrasound in Med. & Biol., vol. 38, No. 7, pp. 1298-1305, 2012.
New doxorubicin-loaded phospholipid microbubbles for targeted tumor therapy: Part I—Formulation development and in-vitro characterization by Steliyan Tinkov et al. from Journal of Controlled Release 143 (2010) 143-150.
Membrane Fluidity and Temperature Perception by Norio Murata et al. from Plant Physiol. (1997) 115:835-879.
Definity, Vial for (Perflutren Lipid Microsphere) Injectable Suspension, Initial U.S. Approval: 2001, Revised: Apr. 2013.
Acta Biomaterialia, 2010, vol. 6, 3542-3549.
Colloids and Surfaces B: Biointerfaces, 2004, vol. 35, 209-223.
Langmuir, 2010 vol. 26, No. 20, 15726-15729.
Using Fluidity Regulation to Control Size Distribution of Lipid-coated Bubbles, Chung-Hsin Wang et al., 2011 IEEE International Ultrasonics Symposium Proceedings, 2428-2431.

* cited by examiner

Primary Examiner — Michael G Hartley
Assistant Examiner — Melissa Perreira
(74) Attorney, Agent, or Firm — Chang-Hsing Liang

(57) ABSTRACT

A method of producing lipid-based micro/nano bubbles includes steps of (a) preparing a lipid mixture including one or more first lipids with different phase transition temperature, and a second lipid bonding with a hydrophilic polymer moiety or molecules capable of getting across a lipid membrane and decreasing van der Waals forces between lipid bilayers; (b) emulsifying the lipid mixture with a solvent, to form a transparent lipid carrier solution; (c) placing the transparent lipid carrier solution in a closed vessel with halo-substituted hydrocarbon; (d) manipulating temperature of the transparent lipid carrier solution to be close to a main phase transition temperature thereof; and (e) agitating in a mechanical manner the vessel containing the transparent lipid carrier solution to form micro/nano bubbles within the closed vessel. This method contributes to form micro/nano bubbles with desired diameters in a way of optimal material utilization efficiency.

14 Claims, 9 Drawing Sheets

METHOD AND DEVICE FOR PRODUCING OPTIMIZED LIPID-BASED MICRO/NANO-BUBBLES

CROSS-REFERENCE TO RELATED APPLICATIONS

This application claims the benefit of the filing date of Taiwan Patent Application No. 102115967, filed on May 3, 2013, in the Taiwan Intellectual Property Office, the disclosure of which is incorporated herein in its entirety by reference.

BACKGROUND OF THE DISCLOSURE

Field of the Disclosure

The disclosure relates to lipid-based micro/nano-bubbles, and in particular, to a method of preparing lipid-based micro/nano-bubbles with a controlled diameter in a way of an optimal material utilization with an optimal bubble concentration.

Related Art

Micro-bubbles are commonly applied to function as an ultrasound contrast agent in form of fine bubbles with diameter of 1-5 µm encapsulated by a biodegradable material. Such micro-bubble-based ultrasound contrast agent can circulate well in the blood stream and provide a significant echo-enhancement of perfusion in ultrasound imaging. Micro-bubbles have a high degree of echogenicity because of their much lower density (compared with human tissues) and compressible inner. These characteristics allow bubbles to reflect the ultrasound waves and further oscillate with these waves. The echogenicity difference between the gas in the micro-bubbles and the soft tissue structures of the body is so significant that the ultrasound signal intensity may be enhanced by 20-40 dB. Thus, the micro-bubble-based ultrasound contrast agent can be used to image blood perfusion in organs, measure blood flow rate in the heart and other organs. Studies also show that micro-bubbles have the similar characteristics to the contrast mediums of other medical imaging systems for tumor diagnosis.

Another medical application for the micro-bubble-based ultrasound contrast agent is ultrasound molecular imaging. Through targeting ligand-conjugated micro-bubbles to specific biomarkers on target tissues, ultrasound imaging can be used to highlight those tissues, such as tumor, ischemia and inflammation areas, helping physicians achieving early detections of various diseases. The similar application to ultrasound molecular imaging is targeted therapy. Drug is encapsulated in the micro-bubbles to be injected into the blood vessel. Once the micro-bubbles are accumulated remarkably in target tissues, drug release is actively triggered by focused ultrasound. Ultrasound causes bubble destruction, which lowers the threshold for cavitation, resulting in micro streaming and increased permeability of cell membranes. In other words, micro-bubbles serve as a vehicle to carry the anti-tumor drug and locally release it when exposed to therapeutic ultrasound, which is referred to as ultrasound-triggered drug release. Several studies also showed the possibility of using micro/nano-bubbles to deliver genes into live cells.

However, as currently used micro-bubbles are relatively bigger in diameter and unstable in blood circulation. Those micro-bubbles are hard to reach a sufficient accumulation in target tissue in such a limited time. Lack of a preparation method with optimal material utilization efficiency (referred to lipid-to-bubble conversion ratio) also slows down the developments of functional micro-bubbles, such as ligand-conjugated, drug-encapsulated and nanoparticle-loaded micro-bubbles. Low material utilization efficiency results in a great loss of those costly functional compounds that makes the commercialization of functional micro-bubbles difficult. Therefore, it would be greatly desirable to have micro-bubbles which can be well controlled in diameter, stability, and material utilization efficiency (optimal material utilization efficiency).

SUMMARY OF THE DISCLOSURE

In view of the forgoing problems, the disclosure discloses a method of producing lipid-based micro/nano bubbles (including ultrasound contrast micro-bubbles as well), in which the fluidity of the lipid membrane and the main phase transition temperature of the transparent lipid carrier solution are determined by the composition of the lipid mixture, and the closed vessel containing the lipid carrier is mechanically agitated at the temperature around the main phase transition temperature of lipid carrier, thus forming the micro-bubbles in a way of an optimal material utilization efficiency. The size distribution and circulating stability of micro/nano bubbles can be improved through the fluidity regulation in the same time.

In one aspect, this disclosure provides a method of producing lipid-based micro/nano bubbles. The method includes steps of (a) preparing a lipid mixture including one or more first lipids with different phase transition temperature, and a second lipid bonding with a hydrophilic polymer moiety or molecules capable of getting across a lipid membrane and decreasing van der Waals forces between lipid bilayers; wherein each of the first lipids includes a hydrophobic C8-C30 end, and the second lipid is additionally bonding with a hydrophilic long chain polymer moiety of molecular weight of 200-200,000; (b) emulsifying the lipid mixture with a solvent by mechanical means to form a transparent lipid carrier solution; (c) placing the transparent lipid carrier solution in a closed vessel further with a predetermined gas or hydrophobic molecules; (d) manipulating temperature of the transparent lipid carrier solution to be close to the main phase transition temperature of the transparent lipid carrier solution; and (e) agitating in a mechanical manner the closed vessel containing the transparent lipid carrier solution to form micro/nano bubbles within the closed vessel.

In another aspect, this disclosure provides a lipid mixture including: (a) one or more first lipids with different main phase transition temperatures, wherein each of the first lipids includes a C8-C30 alkyl chain, the C8-C30 alkyl chain selected from the group consisting of linear alkyl chain, alkenyl chain, alkylnyl chain, a fluoroalkyl chain, branched alkyl chain, and the combination thereof; and (b) a second lipid bonding with a hydrophilic polymer moiety or molecules capable of getting across a lipid membrane and decreasing van der Waals forces between lipid bilayers, wherein the second lipid includes alkyl chain as that of the first lipids and is additionally bonding with a hydrophilic long chain polymer moiety of molecular weight of 200-200,000; wherein the lipid mixture is arranged such that the main phase transition temperature or the lipid membrane fluidity of a transparent lipid carrier solution including the lipid mixture is capable to be manipulated through manipulating the mixing ratio of the lipid mixture, so as to form micro/nano bubbles with desired diameters in a way of optimal material utilization efficiency by agitating the transparent lipid carrier solution under a temperature closed to the main phase transition temperature of the lipid carrier in a mechanical manner.

In yet another aspect, this disclosure provides another lipid mixture including: (a) one or more first lipids with different main phase transition temperatures, wherein each of the first lipids includes a C8-C30 alkyl chain, the C8-C30 alkyl chain selected from the group consisting of linear alkyl chain, alkenyl chain, alkylnyl chain, a fluoroalkyl chain, branched alkyl chain, and the combination thereof; (b) a second lipid bonding with a hydrophilic polymer moiety, wherein the second lipid includes alkyl chain as that of the first lipids and is additionally bonding with a hydrophilic long chain polymer moiety of molecular weight of 200-200,000; and (c) molecules capable of getting across a lipid membrane and decreasing van der Waals forces between bilayers; wherein the lipid mixture is arranged such that the lipid membrane fluidity of a transparent lipid carrier solution including the lipid mixture is capable to be manipulated through manipulating the mixing ratio of the molecules capable of getting across a lipid membrane in the lipid mixture, so as to form micro/nano bubbles with desired diameters in a way of optimal material utilization efficiency by agitating the transparent lipid carrier solution under a temperature lower than the main phase transition temperature of the lipid mixture in a mechanical manner.

In further another aspect, this disclosure provides a device for producing lipid-based micro/nano bubbles where a lipid mixture is used as a starting material to be dissolved in distilled water, saline, or buffered saline, the lipid mixture comprising one or more first lipids with different main phase transition temperatures, and a second lipid bonding with a hydrophilic polymer moiety or molecules capable of getting across a lipid membrane and decreasing van der Waals forces between lipid bilayers; wherein each of the first lipids includes a C8-C30 alkyl chain, the C8-C30 alkyl chain selected from the group consisting of linear alkyl chain, alkenyl chain, alkylnyl chain, a fluoroalkyl chain, branched alkyl chain, and the combination thereof; and the second lipid includes alkyl chain as that of the first lipids and is additionally bonding with a hydrophilic long chain polymer moiety of molecular weight of 200-200,000.

The above device includes: (a) a temperature controlling unit, for manipulating a temperature of the transparent lipid carrier solution to be close to a main phase transition temperature of the transparent lipid carrier solution; and (b) a mechanical agitator, for providing mechanical agitations on the transparent lipid carrier solution; wherein the device is arranged such that the mechanical agitator is used to agitating a closed vessel containing the transparent lipid carrier solution having a temperature close to the main phase transition temperature to form the lipid-based micro/nano bubbles in the closed vessel.

This disclosure is advantageous particularly in that the cost for manufacturing the micro/nano bubbles can be reduced greatly by manipulating the composition of the lipid mixture and mechanically agitating the vessel containing the lipid carrier at the temperature close to the main phase transition temperature of lipid carrier. Besides, the size or diameter of the micro/nano bubbles can also be determined as required by modifying the composition of the lipid mixture and the temperature at which the lipid carrier is mechanically agitated. Once the composition is incorporated with high phase transition temperature materials, the circulating stability or the retention time of encapsulated drug can also be improved. Therefore, this disclosure may contribute significantly to applications of non-linear ultrasound contrast imaging, ultrasound molecular imaging and targeted therapy where micro/nano-bubbles are involved. Further, a micro/nano bubble agent with optimal concentration may show its usefulness in transdermal delivery applications because of its fine characteristics in the capabilities of smearing over the skin and oscillating with ultrasound waves to improve the permeability of cuticles. A optimized bubble agent fabricated by engineered lipid surfactants could be extensively applied to cleaning applications such as cloths laundering, tooth washing or semi-conductor washing processes.

The characteristics, realization and functions of the disclosure are disclosed in the following description with reference to the preferred exemplified embodiments and the accompanying drawings

BRIEF DESCRIPTION OF THE DRAWINGS

This disclosure will become more fully understood from the detailed description given herein below for illustration only, and thus not limitative of this disclosure, wherein.

DETAILED DESCRIPTION OF THE DISCLOSURE

Figure 1:
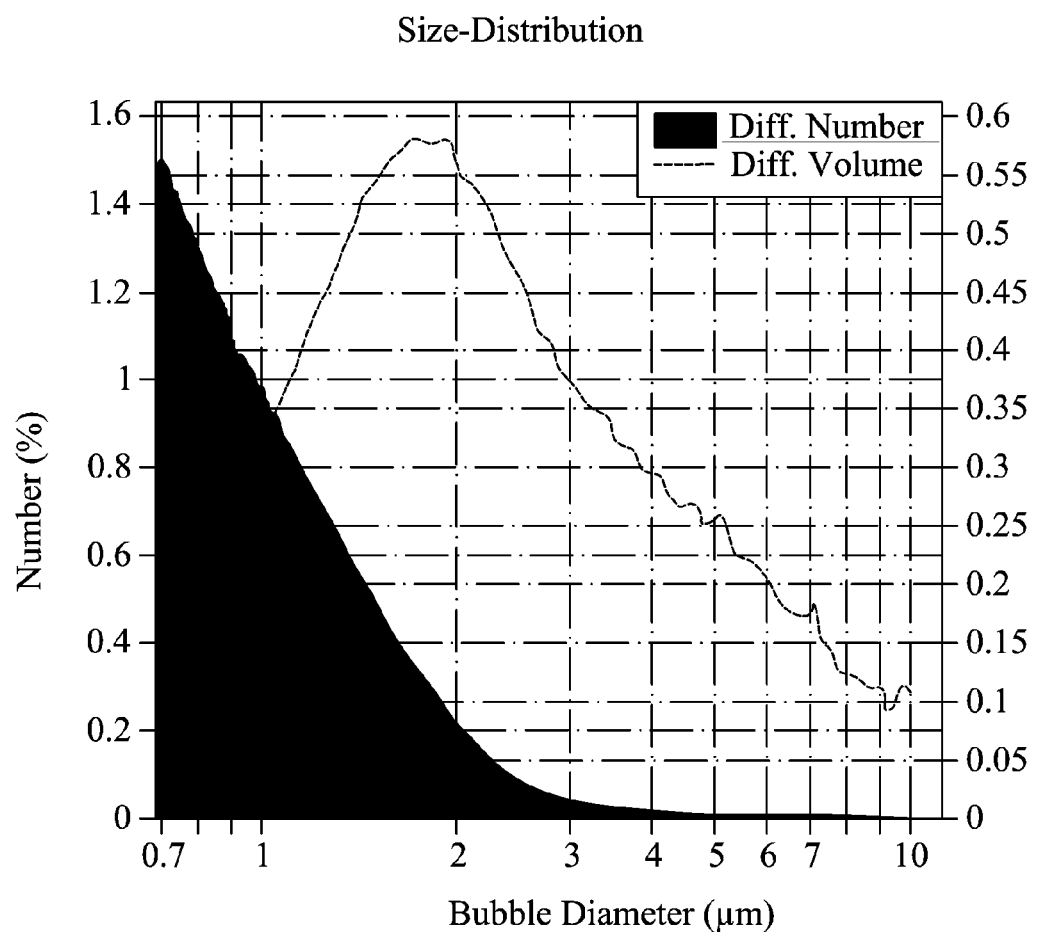
FIG. 1 is the size distribution of DSPC-based micro/nano bubbles of this disclosure from Coulter counter particle analyzer (USP compliant)

In the following description of preferred embodiments, reference is made to the accompanying drawings which form a part hereof, and in which it is shown by way of illustration specific embodiments in which the disclosure can be practiced. It is to be understood that other embodiments can be used and structural changes can be made without departing from the scope of the embodiments of this disclosure.

Mechanical agitation is involved in a method of producing lipid-based micro/nano bubbles in this disclosure. A lipid mixture having a lipid membrane is agitated to disrupt the original membrane structure, followed by reforming the membrane to encapsulate the introduced gas in the innermost layer to form micro/nano bubbles. The membrane fluidity of lipid membranes indicates the ability of lipids moving on the membrane (refers to the ease of membrane disruption/reformation), which greatly influences the micro/nano bubbles formed by the mechanical agitation in throughput, size, and size distribution. In practice, the ultrasound contrast micro-bubbles above 8 μm in size will clog up lung capillaries. Therefore, it is important to control the size of the micro-bubbles properly. However, it is difficult to manipulate both the size and size distribution of the ultrasound contrast micro-bubbles, so bubbles above a predetermined diameter in size have to be removed finally as in prior art. Several clinical products which have around 2~5% micro-bubbles larger than 10 μm have raised the concerns of safety issues in clinical uses.

In one embodiment, the method of producing ultrasound contrast micro/nano bubbles includes the steps below.

As the initial step, a lipid mixture is prepared. Note that the lipid mixture could be prepared with a green manufacturing process which uses only glycerol (propane-1,2,3-triol) or propylene glycol (propane-1,2-diol) as the initial solvent to mix and disperse all lipid materials (the solution temperature should be manipulated to the temperature closed to the main phase transition temperature of the lipid mixture). Compared with prior arts, this clean manufacturing process avoids the use of toxic organic solvents such as methanol, toluene and chloroform.

The lipid mixture includes (a) one or more first lipids with different main phase transition temperatures and (b) a second lipid bonding with a hydrophilic moiety. Each of the first lipids includes a hydrophobic C8-C30 end. Alternatively, one or more categories of molecules capable of getting across a lipid membrane and decreasing van der Waals forces between lipid bilayers may be added for regulating the main phase transition temperature of the lipid mixture or further replaced for the second lipid. Besides, a solvent exclusive of water, i.e., non-water solvent, may be also added to reduce the interactions between lipids for the same purpose of regulating the main phase transition temperature of the lipid mixture. The hydrophobic C8-C30 ends may be, but not limited to, a linear or branched alkyl chain, alkenyl chain, alkylnyl chain or a fluoroalkyl chain or a combination thereof. Polymers with multiple hydrophobic C8-C30 ends could be also used as the first lipids.

Further, the first lipid may be, for example:
1,2-dimyristoyl-sn-glycero-3-phosphocholine (DMPC),
1,2-dimyristoyl-sn-glycero-3-phosphoethanolamine (DMPE),
1,2-dimyristoyl-sn-glycero-3-phospho-(1'-rac-glycerol) (DMPG),
1,2-dimyristoyl-sn-glycero-3-phosphoserin (DMPS),
1,2-dimyristoyl-sn-glycero-3-phosphate (DMPA),
1,2-dipalmitoyl-sn-glycero-3-phosphocholine (DPPC),
1,2-dipalmitoyl-sn-glycero-3-phosphate (DPPA),
2-dipalmitoyl-sn-glycero-3-phosphserine (DPPS),
1,2-dipalmitoyl-sn-glycero-3-phospho-(1'-rac-glycerol) (DPPG),
1,2-dipalmitoyl-sn-glycero-3-phosphoethanolamine (DPPE),
1,2-distearoyl-sn-glycero-3-phosphocholine (DSPC),
1,2-distearoyl-sn-glycero-3-phospho-(1'-rac-glycerol) (DSPG),
1,2-distearoyl-sn-glycero-3-phosphoethanolamine (DSPE),
1,2-distearoyl-sn-glycero-3-phosphate (DSPA),
1,2-distearoyl-sn-glycero-3-phosphserine (DSPS),
1,2-dioleoyl-3-trimethylammonium-propane (DOTAP),
1,2-dioleoyl-sn-glycero-3-phosphocholine (DOPC),
1,2-dioleoyl-sn-glycero-3-phosphoethanolamine (DOPE),
1,2-dioleoyl-sn-glycero-3-phosphate (DOPA),
1,2-dioleoyl-sn-glycero-3-phospho-(1'-rac-glycerol) (DOPG),
1,2-dioleoyl-sn-glycero-3-phosphserine (DOPS),
1,2-dipalmitoyl-3-trimethylammonium-propane (DPTAP),
1,2-distearoyl-3-trimethylammonium-propane (DSTAP), dimethyldioctadecylammonium bromide (DMDDA),
1,2-dipalmitoyl-sn-glycero-3-phosphoethanolamine-N-diethylenetriaminepentaacetic acid (DPPE-DTPA),
1,2-distearoyl-sn-glycero-3-phosphoethanolamine-N-diethylenetriaminepentaacetic acid (DSPE-DTPA),
myristic acid, palmitic acid, stearic acid, oleic acid, tocopherols, tocotrienols, ascorbyl palmitate,
SPAN (Registered Trademark), Loxiol (Registered Trademark), Atlas™, Arlacel™, Emcol (Registered Trademark) or a combination thereof or derived polymers thereof.

Among others, combination of 1,2-dipalmitoyl-sn-glycero-3-phosphocholine (DPPC) and 1,2-distearoyl-sn-glycero-3-phospho-(1'-rac-glycerol) (DSPG) is used as the first lipid in this embodiment.

It should be understood that the main phase transition (solid to liquid) temperature of DPPC is 41 Celsius degree, while that of DSPG is 55 Celsius degree. Lipid with higher phase transition temperature is advantageous in reducing size (diameter) and increasing stability of the resultant micro/nano bubbles. The second lipid has a similar carbon chain structure (C8-C30, backbone) to the above first lipid and the second is additionally bonding with a hydrophilic long chain polymer moiety of molecular weight of 200-200000. The hydrophilic long chain polymer moiety may be for example polyethylene glycol (PEG), polypropylene glycol, polyoxyethylene, polyvinylalcohol, polyvinylpyrrolidone and related copolymers, and peptide, deoxyribonucleic acid (DNA), or ribonucleic acid (RNA) or a combination thereof.

The second lipid may be, but not limited to,
1,2-dipalmitoyl-sn-glycero-3-phosphoethanolamine-N-[methoxy(polyethylene glycol)-2000] (DPPE-PEG2000),
1,2-dipalmitoyl-sn-glycero-3-phosphoethanolamine-N-[methoxy(polyethylene glycol)-3000] (DPPE-PEG3000),
1,2-dipalmitoyl-sn-glycero-3-phosphoethanolamine-N-[methoxy(polyethylene glycol)-3000] (DPPE-PEG5000),
1,2-distearoyl-sn-glycero-3-phosphoethanolamine-N-[methoxy(polyethylene glycol)-5000] (DSPE-PEG2000),
1,2-distearoyl-sn-glycero-3-phosphoethanolamine-N-[methoxy(polyethylene glycol)-5000] (DSPE-PEG3000),
1,2-distearoyl-sn-glycero-3-phosphoethanolamine-N-[methoxy(polyethylene glycol)-5000] (DSPE-PEG5000),
polyoxyethylene stearates, polyethylene glycol stearates, TWEEN (Registered Trademark), Myrj™, Atlas™, d-alpha-tocopheryl polyethylene glycol 1000 succinate (Vitamin E TPGS), antibody-conjugated PEG-ylated lipid, peptide-conjugated PEG-ylated lipid, DNA-conjugated PEG-ylated lipid, RNA-conjugated PEG-ylated lipid, biotin-modified PEG-ylated lipid, maleimide-modified PEG-ylated lipid, amine-modified PEG-ylated lipid, and the combination thereof or the derived polymers thereof. In this embodiment, polyethylene glycol 40 stearates (PEG40S) are employed.

The molecule, which is able to get across the lipid membrane and to decrease van der Waals forces between lipid bilayers, may be but not limited to, polyethylene glycol, peptide, albumin, amino acid, sugar alcohols, butane-1,3-diol, propane-1,2,3-triol, propane-1,2-diol, propane-1,3-diol, propan-1-ol, ethane-1,2-diol, ethanol, methanol and dimethyl sulfoxide, or a combination thereof. Propane-1,2,3-triol (glycerol) is used in this embodiment for improving the membrane fluidity and ability of the lipid membrane to reconstruct itself. Particularly, some chemicals listed above like methanol and ethanol may greatly increase the final throughput of the micro-bubbles under the temperature far below the original main phase transition temperature (determined in water) of the lipid mixture even with a concentration of the range of 0.1 to 2 wt %.

As the second step, the lipid mixture including DSPG, DPPC, and PEG40S blended with a solvent such as normal saline or buffered saline. For example the mixture of DSPG, DPPC, and PEG40S is blended with a solvent of phosphate buffer saline containing 1 wt % of glycerol and a bilayer lipid membrane will be formed. In particular, since PEG40S functions to increases the membrane fluidity of the lipid membrane, the bilayer lipid membrane may be disrupted and reconstructed more easily during the followed agitation to form a monolayer structure, thereby encapsulating the introduced gas and increasing the final throughput of the micro/nano bubbles. The molecule capable of getting across the lipid membrane and decreasing the van der Waals forces between lipid bilayers, i.e., glycerol in this embodiment, functions similarly to PEG40S. Besides, DSPG with the higher main phase transition temperature in the first lipid serves to decrease the membrane fluidity of the lipid membrane and stabilize the resultant micro-bubbles.

As the third step, the resultant solution formed by blending those lipid materials with the solvent is then mechanically emulsified until a transparent lipid carrier solution is formed. Sonication, high-speed agitation, high-pressure homogenization or membrane filtration may be employed to mechanically emulsify the lipid mixture within the solvent. In this embodiment, a bath sonicator is used for sonication, and the transparent lipid carrier solution is adjusted to have a concentration of the lipid carrier of 3 mg/mL and a temperature of 20 Celsius degree. This step is directed to dispersing the lipid materials in the transparent lipid carrier solution and decreasing the particle size of the lipid carrier, thus facilitating the subsequent preparation of the micro/nano bubbles. Note that the lipid concentration for fabricating nano bubbles (bubbles with size less than 1 μm) should be typically higher than 0.5 mg/mL. As the fourth step, the transparent lipid carrier solution used as the lipid carrier is placed in a closed vessel with a proper size. In this example, 1 mL of the transparent lipid carrier solution is added into the 1.8 mL closed vessel. Preferably, 0.5-1.0 mL of the transparent lipid carrier solution is used.

As the fifth step, the closed vessel is vacuumed and filled with a predetermined gas such as halo-substituted hydrocarbon (perfluorocarbon), inert gas, Sulfur hexafluoride, nitrogen, oxygen, air, or a combination thereof. The predetermined gas could also be introduced into the vessel by sealing the vessel in a closed system or environment that contained with the predetermined gas or flushing/purging the vessel with the predetermined gas. Hydrophobic molecules with specific functionalities could be further added into the closed vessel in this step together with the predetermined gas. The hydrophobic molecules may be, but not limited to, specific drug(s) to be incorporated into the lipid membrane of micro/nano bubbles for medical applications, such as ultrasound-triggered drug release, ultrasound-assisted tumor therapy and micro-bubble-based blood brain barrier disruption. It will be appreciated that a person skilled in the art can understand the way for filling the predetermined gas and it will not be addressed particularly here for avoiding unnecessary confusion.

As the sixth step, temperature of the transparent lipid carrier solution is manipulated to be approximate to a main phase transition temperature thereof by water bath for example, thus improving the membrane fluidity, ability of the lipid membrane to reconstruct itself, and the throughput of the micro-bubbles. For example, given the transparent lipid carrier solution with the main phase transition temperature of 46 Celsius degree composed of DPPC, DSPG, and PEG40S in a ratio of 1:1:1 (w/w/w), the reaction temperature of 43 Celsius degree at the next step will result in a throughput of micro/nano bubbles three times higher than that of 20 Celsius degree. In short, manipulating the temperature of the transparent lipid carrier solution is favorable in preparing the micro/nano bubbles in a way having optimal material utilization efficiency. However, it is noted that the temperature of the transparent lipid carrier solution may be manipulated to a temperature closed but higher than its main phase transition temperature thereof, in case of a decreased temperature of the transparent lipid carrier solution during the subsequent agitating process in a mechanical manner. For example, if the main phase transition temperature of the transparent lipid carrier solution composed of DSPC, DSPE-PEG2000 in a ratio less than 10:4 (w/w) is 56 Celsius degree, since the temperature during the subsequent agitating process in a mechanical manner can only be maintained at about 50 Celsius degree, the transparent lipid carrier solution is desirably heated to 60 Celsius degree in advance for obtaining the high-throughput micro/nano bubbles in a way having an optimal material utilization efficiency (the throughput of the micro-/nano bubbles may be up to 4E+10 bubbles/mL). Through the use of a high transition temperature material, so as DSPC, the average size could be reduced to the range of 400 to 700 nm (depends on compositions).

FIG. 1 the size distribution of DSPC-based micro/nano bubbles of this disclosure from Coulter counter particle analyzer (USP compliant).

As the seventh step, the closed vessel containing the transparent lipid carrier solution is agitated in a mechanical manner to form ultrasound contrast micro/nano bubbles within the closed vessel. The mechanical agitation is realized by for example sonication, manual shaking, high-speed mechanical agitation, microfluidic device/T-focusing, or co-axial electrohydrodynamic atomization (CEHDA) micro-bubbling. A mechanical agitator is used at 4550 rpm for 45 seconds in this embodiment, by which 99.9% of the resultant micro-bubbles have a diameter less than 8 μm. Preferably, the diameter is ranging from 0.2 μm to 8 μm. The way of high-speed mechanical agitation is favorable because the size and size distribution of the micro-bubbles can be controlled effectively. Table I lists the average diameter (average from the range of 0.7 to 18 μm) of the micro-bubbles under different compositions of the transparent lipid carrier solution. The peak diameters of several listed compositions may be much smaller than the average diameters determined from the measuring range of 0.7 to 18 μm.

TABLE I

| No. | DPPC:DSPG:PEG40S (w/w/w) | Average diameter (μm) |
| --- | --- | --- |
| 1 | 10:4:1 | 0.931 ± 0.007 |
| 2 | 10:4:2 | 1.083 ± 0.006 |
| 3 | 10:4:3 | 1.171 ± 0.114 |
| 4 | 14:0:2 | 1.814 ± 0.015 |
| 5 | 14:0:4 | 2.368 ± 0.061 |
| 6 | 14:0:6 | 2.861 ± 0.046 |

Alternatively, the lipid mixture includes (a) one or more first lipids with different main phase transition temperatures, wherein each of the first lipids includes a C8-C30 alkyl chain; (b) a second lipid bonding with a hydrophilic polymer moiety, wherein the second lipid includes alkyl chain as that of the first lipids; and (c) at least one category of molecules capable of getting across a lipid membrane and decreasing van der Waals forces between lipid bilayers. The C8-C30 alkyl chain may be, but not limited to, a linear or branched alkyl chain, alkenyl chain, alkylnyl chain, a fluoroalkyl group, or a combination thereof. Polymers with multiple hydrophobic C8-C30 ends could be also used as the first lipids.

Further, the first lipid may be, for example,
1,2-dimyristoyl-sn-glycero-3-phosphocholine (DMPC),
1,2-dimyristoyl-sn-glycero-3-phosphoethanolamine (DMPE),
1,2-dimyristoyl-sn-glycero-3-phospho-(1'-rac-glycerol) (DMPG),
1,2-dimyristoyl-sn-glycero-3-phosphoserin (DMPS),
1,2-dimyristoyl-sn-glycero-3-phosphate (DMPA),
1,2-dipalmitoyl-sn-glycero-3-phosphocholine (DPPC),
1,2-dipalmitoyl-sn-glycero-3-phosphate (DPPA),
2-dipalmitoyl-sn-glycero-3-phosphserine (DPPS),
1,2-dipalmitoyl-sn-glycero-3-phospho-(1'-rac-glycerol) (DPPG),
1,2-dipalmitoyl-sn-glycero-3-phosphoethanolamine (DPPE),
1,2-distearoyl-sn-glycero-3-phosphocholine (DSPC),
1,2-distearoyl-sn-glycero-3-phospho-(1'-rac-glycerol) (DSPG),
1,2-distearoyl-sn-glycero-3-phosphoethanolamine (DSPE),
1,2-distearoyl-sn-glycero-3-phosphate (DSPA),
1,2-distearoyl-sn-glycero-3-phosphserine (DSPS),
1,2-dioleoyl-3-trimethylammonium-propane (DOTAP),
1,2-dioleoyl-sn-glycero-3-phosphocholine (DOPC),
1,2-dioleoyl-sn-glycero-3-phosphoethanolamine (DOPE),
1,2-dioleoyl-sn-glycero-3-phosphate (DOPA),
1,2-dioleoyl-sn-glycero-3-phospho-(1'-rac-glycerol) (DOPG),
1,2-dioleoyl-sn-glycero-3-phosphserine (DOPS),
1,2-dipalmitoyl-3-trimethylammonium-propane (DPTAP),
1,2-distearoyl-3-trimethylammonium-propane (DSTAP),
dimethyldioctadecylammonium bromide (DMDDA),
1,2-dipalmitoyl-sn-glycero-3-phosphoethanolamine-N-diethylenetriaminepentaacetic acid (DPPE-DTPA),
1,2-distearoyl-sn-glycero-3-phosphoethanolamine-N-diethylenetriaminepentaacetic acid (DSPE-DTPA), myristic acid, palmitic acid, stearic acid, oleic acid, tocopherols, tocotrienols, ascorbyl palmitate, SPAN (Registered Trademark), Loxiol (Registered Trademark), Atlas™, Arlacel™, Emcol (Registered Trademark) or a combination thereof or derived polymers thereof.

The second lipid has a similar carbon chain structure (C8-C30, backbone) to the above first lipid and is bonding with a hydrophilic long chain polymer moiety of molecular weight of 200-200,000. The hydrophilic long chain polymer moiety may be for example polyethylene glycol (PEG), polypropylene glycol, polyoxyethylene, polyvinylalcohol, polyvinylpyrrolidone and related copolymers, and peptide, deoxyribonucleic acid (DNA), or ribonucleic acid (RNA) or a combination thereof.

The second lipid may be, but not limited to,
1,2-dipalmitoyl-sn-glycero-3-phosphoethanolamine-N-[methoxy(polyethylene glycol)-2000] (DPPE-PEG2000),
1,2-dipalmitoyl-sn-glycero-3-phosphoethanolamine-N-[methoxy(polyethylene glycol)-3000] (DPPE-PEG3000),
1,2-dipalmitoyl-sn-glycero-3-phosphoethanolamine-N-[methoxy(polyethylene glycol)-3000] (DPPE-PEG5000),
1,2-distearoyl-sn-glycero-3-phosphoethanolamine-N-[methoxy(polyethylene glycol)-5000] (DSPE-PEG2000),
1,2-distearoyl-sn-glycero-3-phosphoethanolamine-N-[methoxy(polyethylene glycol)-5000] (DSPE-PEG3000),
1,2-distearoyl-sn-glycero-3-phosphoethanolamine-N-[methoxy(polyethylene glycol)-5000] (DSPE-PEG5000),
polyoxyethylene stearates, polyethylene glycol stearates, TWEEN (Registered Trademark), Myrj™, Atlas™, d-alpha-tocopheryl polyethylene glycol 1000 succinate (Vitamin E TPGS), antibody-conjugated PEG-ylated lipid, peptide-conjugated PEG-ylated lipid, DNA-conjugated PEG-ylated lipid, RNA-conjugated PEG-ylated lipid, biotin-modified PEG-ylated lipid, maleimide-modified PEG-ylated lipid, amine-modified PEG-ylated lipid, and the combination thereof or the derived polymers thereof.

The molecule which is able to pass through the lipid membrane and functions to decrease van der Waals forces between lipid bilayers may be, but not limited to, polyethylene glycol, peptide, albumin, amino acid, sugar alcohols, butane-1,3-diol, propane-1,2,3-triol, propane-1,2-diol, propane-1,3-diol, propan-1-ol, ethane-1,2-diol, ethanol, methanol and dimethyl sulfoxide, or a combination thereof.

By manipulating the composition of the lipid mixture, the membrane fluidity of the transparent lipid carrier solution and ability of the lipid membrane to reconstruct itself is capable to be manipulated through manipulating the mixing ratio of the molecules capable of getting across a lipid membrane in the lipid mixture. Subsequently, the lipid carrier solution is subject to emulsion or mechanical agitation at a temperature lower than the main phase transition temperature of the lipid carrier to form the micro/nano bubbles with desired size of a diameter ranging from 0.2 to 8 μm (not limited to) in a way where optimal material utilization efficiency; wherein the lowered temperature is a temperature ranging from 10 Celsius degree to 60 Celsius degree.

For obtaining the micro/nano bubbles in a way having optimal material utilization efficiency at the temperature close to the main phase transition temperature of the lipid carrier by using mechanical agitation such as sonication, manual shaking, high-speed mechanical agitation, microfluidic device/T-focusing, or co-axial electrohydrodynamic atomization (CEHDA) micro-bubbling, the temperature of the transparent lipid carrier solution may be increased in advance of the mechanical agitation by for example a water bath, dry heat or mechanical agitations themselves, and then be decreased to the temperature around the main phase transition temperature of the lipid carrier, followed by mechanically agitating the entire transparent lipid carrier solution. Alternatively, for example, a heater/cooler system may be combined with a mechanical agitator to facilitate the manipulation of the temperature of the lipid carrier.

Figure 2:
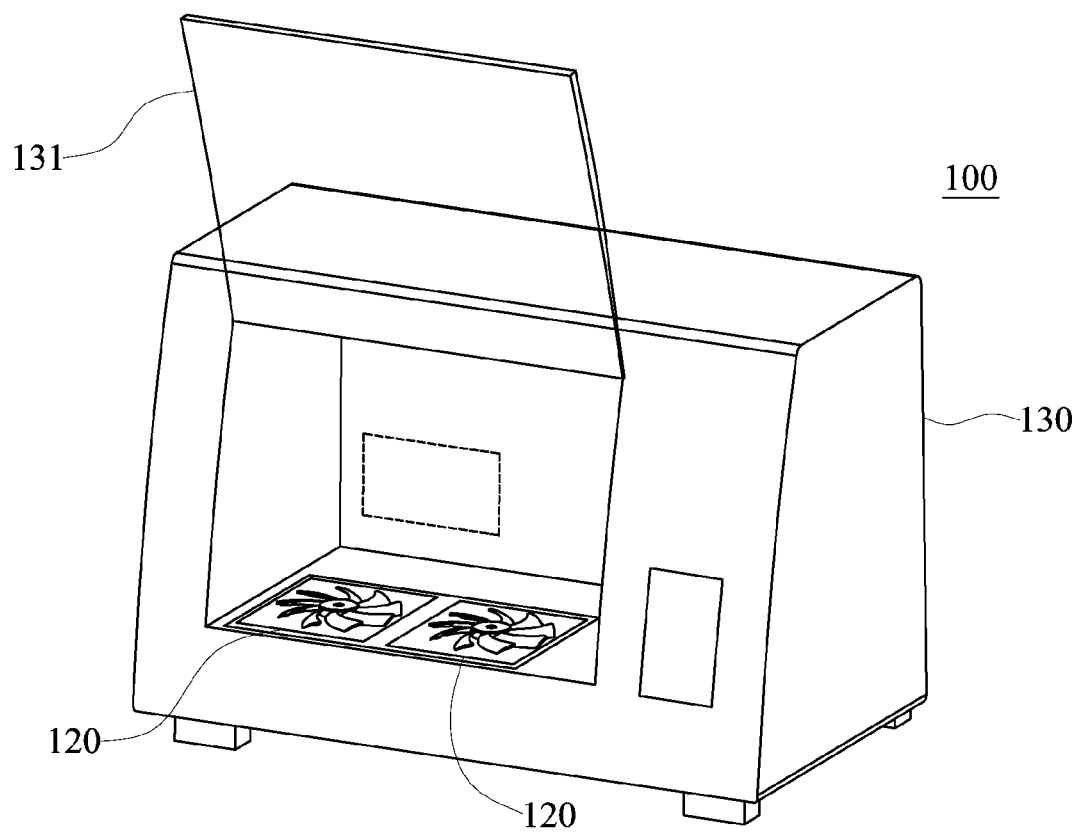
FIG. 2 is a schematic view of a device for producing lipid-based micro/nano-bubbles according to a first embodiment of this disclosure.

FIG. 2 is a schematic view of a device 100 for producing lipid-based micro/nano-bubbles according to a first embodiment of this disclosure.

The lipid mixture as a raw material to be placed in the device 100 includes (a) one or more first lipids with different main phase transition temperatures, each having one or two alkyl chain with 8-30 carbon atoms in length (C8-C30 alkyl chain) and (b) a second lipid bonding with a hydrophilic polymer moiety, or molecules capable of getting across a lipid membrane and decreasing van der Waals forces between lipid bilayers. The second lipid has a similar carbon chain structure (C8-C30, backbone) to the above first lipid, and the second lipid is additionally bonding with a hydrophilic long chain polymer moiety of molecular weight of 200-200,000. The lipid mixture is used as a starting material to be dissolved in distilled water.

Figure 3:
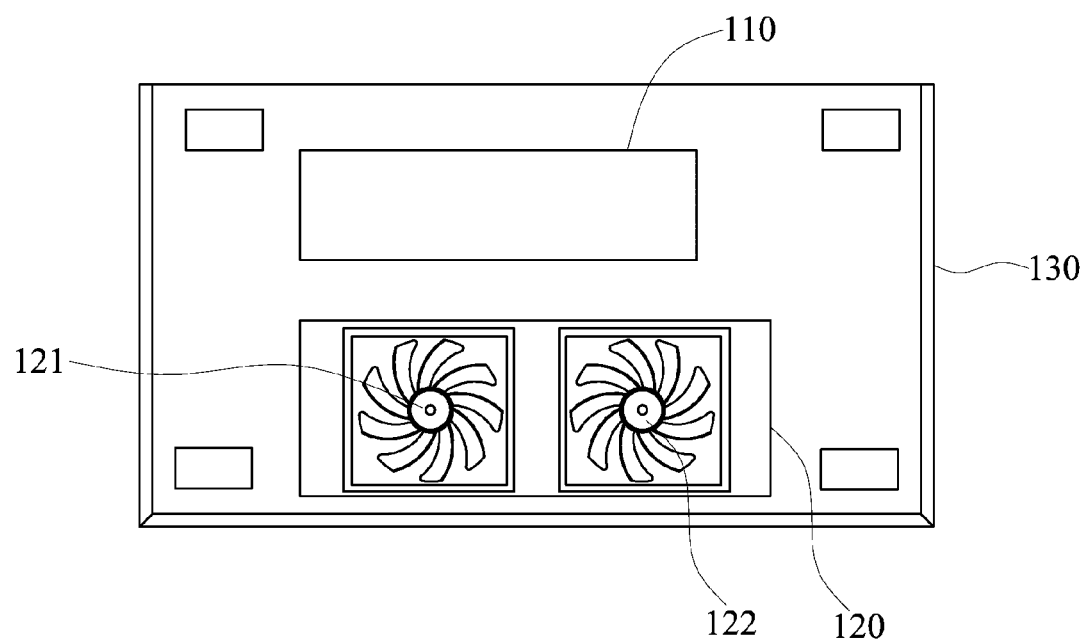
FIG. 3 is a cross-sectional top view of the device of FIG. 2.

FIG. 3 is a cross-sectional top view of the device 100 of FIG. 2. The device 100 includes a mechanical agitator 110 to generate mechanical agitations and a temperature controlling unit 120 to manipulate the temperature of the transparent lipid carrier solution to be closed the main phase transition temperature thereof.

If further agitations from the mechanical agitator 110 are acted on the lipid carrier placed that has been subject to preliminary agitations in a closed vessel 200 clasped by a clamp (not shown), micro/nano bubbles are thus formed therein.

Figure 4:
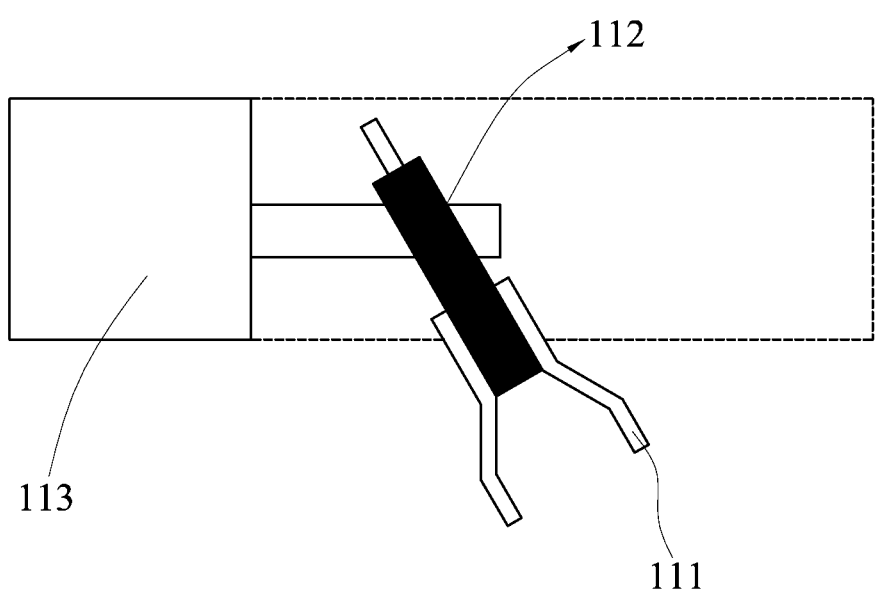
FIG. 4 is a schematic view of a mechanical agitator of this disclosure.
Figure 5:
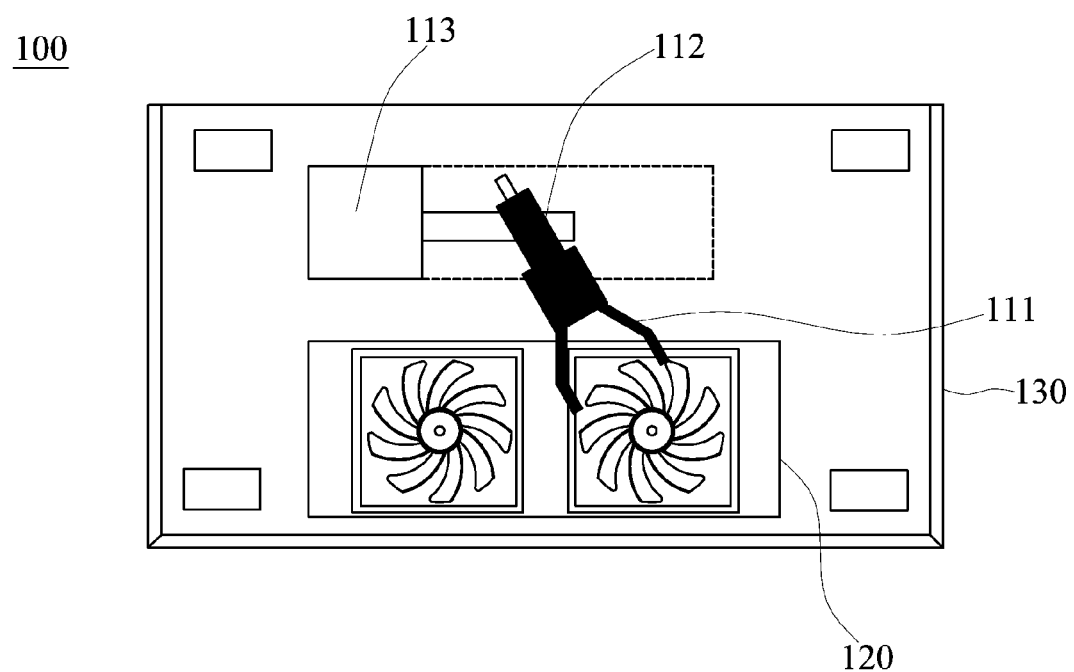
FIG. 5 is a schematic view showing the situation where the mechanical agitator is incorporated with the device for producing lipid-based micro/nano bubbles.
Figure 9:
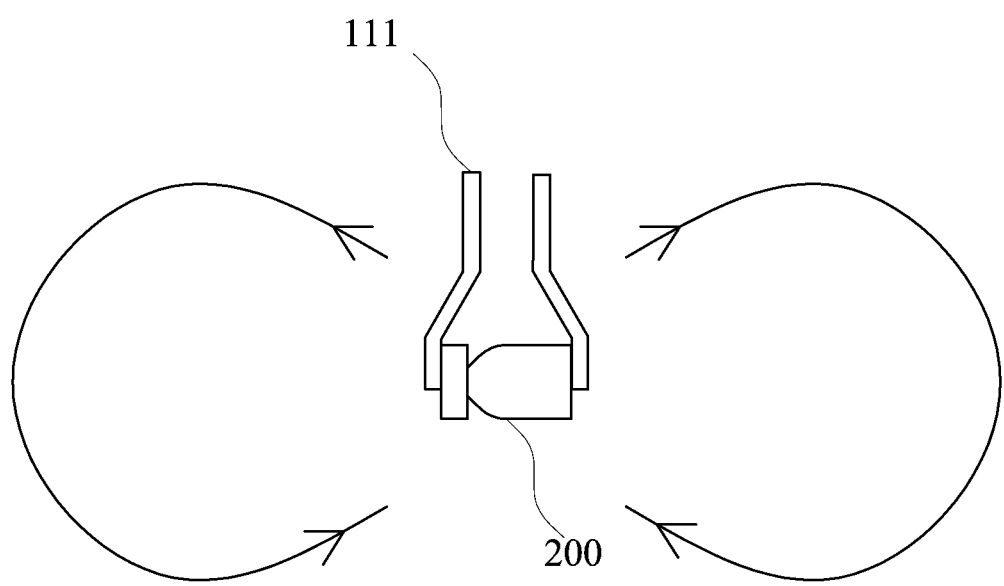
FIG. 9 is a schematic view showing the reciprocation motion of the clamp.

FIG. 4 is a schematic view of the mechanical agitator 110 of this disclosure. The mechanical agitator 110 includes a clamp 111 serving to clasp the closed vessel 200, a lever 112 connected to and allowed to be agitated together with the clamp 111, a motor 113 connected with the lever 112 and providing integrally the clamp 111 and the lever 112 with power for reciprocation, and a fastener (not shown) connected to an end of the lever 112 for restraining the movement thereof. The lever 112 together with the clamp 111 may be reciprocated smoothly to achieve aforementioned mechanical agitations or emulsion when driven by the motor 113 with the restraint of the fastener. FIG. 5 schematically shows the situation where the mechanical agitator 110 is incorporated with the device 100 for producing lipid-based micro/nano bubbles. In this example, the clamp 111 is disposed above the temperature controlling unit 120 to make the manipulation of the temperature controlling unit 120 to the closed vessel 200 containing the lipid mixture and clasped by the clamp 111 more convenient. In other words, even the clamp 111 agitates in a reciprocating way horizontally (either linear or figure-9-shaped as shown in FIG. 9) together with the lever 112 when driven by the motor 113, the closed vessel 200 clasped by the clamp 111 always stays overhead the temperature controlling unit 120 in position regardless of the reciprocation. In this way, a satisfactory temperature controlled performance can be obtained.

Figure 6:
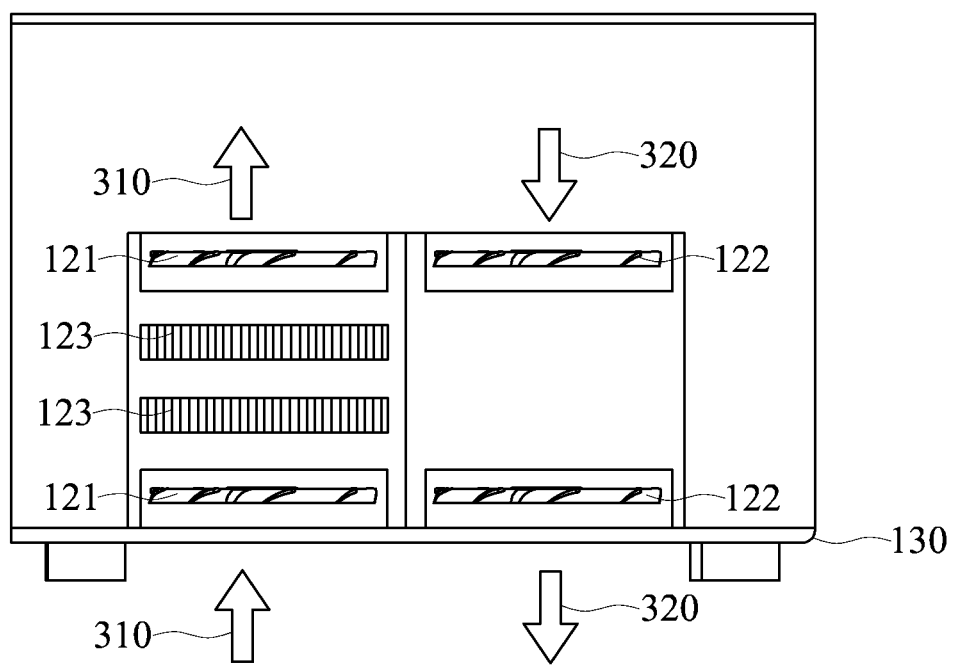
FIG. 6 is a front view of a temperature controlling unit according to one embodiment of this disclosure.
Figure 7:
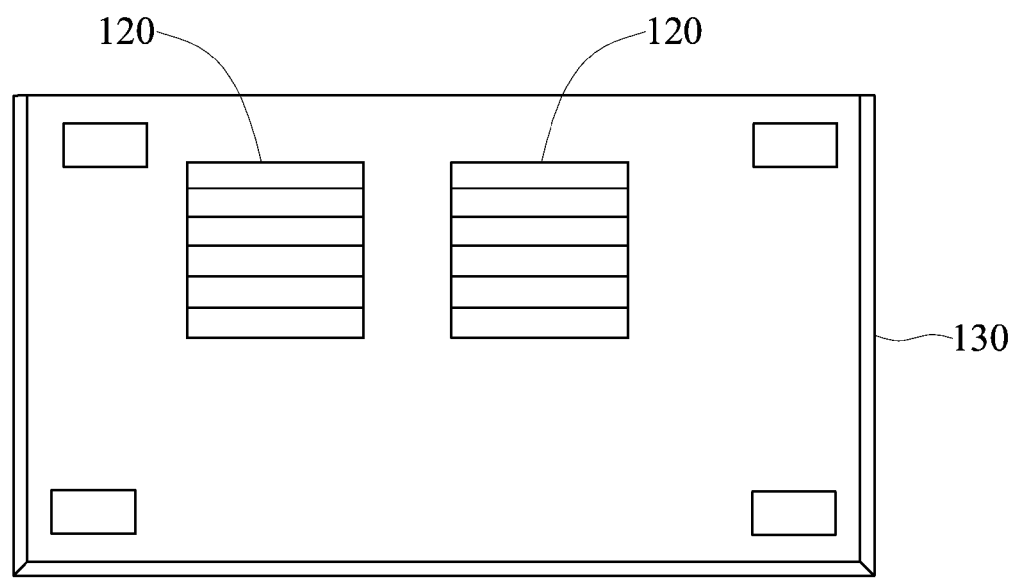
FIG. 7 is a bottom view of the device for producing the lipid-based micro/nano bubbles of this disclosure.

Further, as shown in FIGS. 2 and 3, the device 100 may include a casing 130 for enclosing and accommodating all of the elements together with the lipid mixture. A lid 131 may be provided to the casing 130 for facilitating the take-in or take-out or replacement of the elements. FIG. 6 is a front view of the temperature controlling unit 120 according to one embodiment of this disclosure. The temperature controlling unit 120 disposed within the casing 130 includes a first fan set 121, a second fan set 122, a heating coil 123, and a sensor (not shown). As an alternative, the temperature controlling unit 120 may be incorporated in the clamp 111 or lever 112. FIG. 7 is a bottom view of the device 100 for producing the lipid-based micro/nano bubbles of this disclosure. In FIG. 7, the temperature controlling unit 120 is located on the bottom of the casing 130 as can be observed therefrom.

The first fan set 121 is configured to generate an inlet airflow 310 flowing towards the inside of the casing 130, while the second fan set 122 is configured to generate an outlet airflow 320 flowing towards the outside of the casing 130. The heating coil 123 is configured to heat the inlet airflow 310, and the sensor is configured to detect the temperature within the casing 130.

Figure 8:
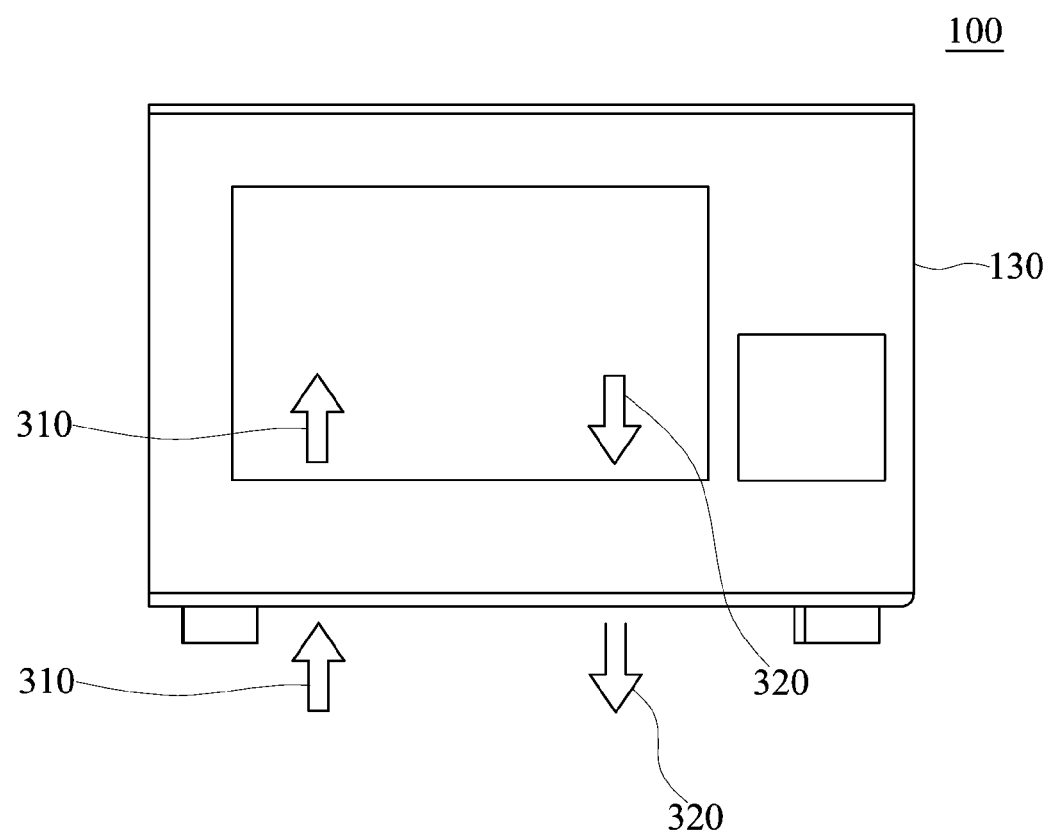
FIG. 8 is a front view of the device for producing the lipid-based micro/nano bubbles where the inlet airflow and outlet airflow are illustrated.

When the temperature within the casing 130 is to be increased to a target temperature, the first fan set 121 and the heating coil 123 are started. However, the second fan set 122 may be optionally started to enhance the thermal convection under this condition. On the contrary, when the temperature within the casing 130 has to be decreased to another target temperature, the second fan set 122 is started with the first fan set 121 optionally. FIG. 8 is a front view of the device 100 for producing the lipid-based micro/nano bubbles of this disclosure where the inlet airflow 310 and outlet airflow 320 are illustrated for better understanding.

In another embodiment, the device 100 may include a dry heating piece (not shown) incorporated in the clamp 111 or lever 112. The heating piece helps the closed vessel 200 with a rapid temperature raise. Also, it is to be noted that the closed vessel 200 containing the transparent lipid carrier solution as the lipid carrier will possibly have a raised temperature due to a severe shaking imparted from the mechanical agitator. Therefore, for example, if the raised temperature is higher than the target temperature, the mechanical shaking may be stopped for a while.

In this disclosure, the fluidity of the lipid membrane and the main phase transition temperature of transparent lipid carrier solution are determined by the composition of the lipid mixture. The vessel 200 containing the lipid carrier is mechanically agitated at the temperature around the main phase transition temperature of lipid carrier, thus forming the micro-bubbles in a way of optimal material utilization efficiency. Hence, this disclosure is advantageous particularly in that the cost for manufacturing the micro/nano bubbles can be reduced greatly.

In addition, size or diameter of the micro/nano bubbles can also be determined as required by the composition of the lipid mixture and the temperature at which the lipid carrier is mechanically agitated.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method of producing lipid-based bubbles, comprising steps of:
preparing a lipid mixture comprising a first lipid, or two or more first lipids with different phase transition temperature, a second lipid bonding with a hydrophilic polymer moiety and optionally one or more molecules capable of getting across a lipid membrane and decreasing van der Waals forces between lipid bilayers; wherein each of the first lipids includes a hydrophobic C8-C30 end, and the hydrophilic polymer moiety has a long chain with molecular weight of 200-200,000;
emulsifying the lipid mixture with an aqueous solvent by mechanical means to form a transparent lipid carrier solution and then adjusting the transparent lipid carrier to 20 Celsius degree;
placing the transparent lipid carrier solution in a closed vessel comprising a predetermined gas;
manipulating temperature of the transparent lipid carrier solution to be close to a main phase transition temperature of the transparent lipid carrier solution while agitating in a mechanical manner the closed vessel containing the transparent lipid carrier solution to form said bubbles within the closed vessel.

2. The method as claimed in claim 1, wherein the hydrophobic C8-C30 end is selected from the groups of linear alkyl chain, alkenyl chain, alkylnyl chain, a fluoroalkyl chain, branched alkyl chain, and the combination thereof.

3. The method as claimed in claim 1, wherein the first lipid is selected from the group consisting of:
1,2-dimyristoyl-sn-glycero-3-phosphocholine,
1,2-dimyristoyl-sn-glycero-3-phosphoethanolamine,
1,2-dimyristoyl-sn-glycero-3-phospho-(1'-rac-glycerol),
1,2-dimyristoyl-sn-glycero-3-phosphserine,
1,2-dimyristoyl-sn-glycero-3-phosphate,
1,2-dipalmitoyl-sn-glycero-3-phosphocholine,
1,2-dipalmitoyl-sn-glycero-3-phosphate,
1,2-dipalmitoyl-sn-glycero-3-phosphserine,
1,2-dipalmitoyl-sn-glycero-3-phospho-(1'-rac-glycerol),
1,2-dipalmitoyl-sn-glycero-3-phosphoethanolamine,
1,2-distearoyl-sn-glycero-3-phosphocholine,
1,2-distearoyl-sn-glycero-3-phospho-(1'-rac-glycerol),
1,2-distearoyl-sn-glycero-3-phosphoethanolamine,
1,2-distearoyl-sn-glycero-3-phosphate,
1,2-distearoyl-sn-glycero-3-phosphserine,
1,2-dioleoyl-3-trimethylammonium-propane,
1,2-dioleoyl-sn-glycero-3-phosphocholine,
1,2-dioleoyl-sn-glycero-3-phosphoethanolamine,
1,2-dioleoyl-sn-glycero-3-phosphate,
1,2-dioleoyl-sn-glycero-3-phospho-(1'-rac-glycerol),
1,2-dioleoyl-sn-glycero-3-phosphserine,
1,2-dipalmitoyl-3-trimethylammonium-propane,
1,2-distearoyl-3-trimethylammonium-propane,
dimethyldioctadecylammonium bromide,
1,2-dipalmitoyl-sn-glycero-3-phosphoethanolamine-N-diethylenetriaminepentaacetic acid,
1,2-distearoyl-sn-glycero-3-phosphoethanolamine-N-diethylenetriaminepentaacetic acid,
myristic acid, palmitic acid, stearic acid, oleic acid, tocopherols, tocotrienols, ascorbyl palmitate, sorbitan esters, glyceryl stearate, glyceryl distearates, glyceryl myristate, glyceryl palmitate glyceryl oleate, polyoxyethylene propylene glyceryl stearates, and the combination thereof or derived polymers thereof.

4. The method as claimed in claim 1, wherein the long chain of the hydrophilic polymer moiety is selected from the group consisting of:
polyethylene glycol, polypropylene glycol, polyoxyethylene, polyvinylalcohol, polyvinylpyrrolidone and related copolymers, peptide, DNA, RNA, and a combination thereof.

5. The method as claimed in claim 1, wherein the second lipid is selected from the group consisting of:
1,2-dipalmitoyl-sn-glycero-3-phosphoethanolamine-N-[methoxy(polyethylene glycol)-2000],
1,2-dipalmitoyl-sn-glycero-3-phosphoethanolamine-N-[methoxy(polyethylene glycol)-3000],
1,2-dipalmitoyl-sn-glycero-3-phosphoethanolamine-N-[methoxy(polyethylene glycol)-5000],
1,2-distearoyl-sn-glycero-3-phosphoethanolamine-N-[methoxy(polyethylene glycol)-2000],
1,2-distearoyl-sn-glycero-3-phosphoethanolamine-N-[methoxy(polyethylene glycol)-3000],
1,2-distearoyl-sn-glycero-3-phosphoethanolamine-N-[methoxy(polyethylene glycol)-5000],
polyoxyethylene stearates, polyethylene glycol stearates, TWEEN (Registered Trademark), Myrj™, Atlas™, d-alpha tocopheryl polyethylene glycol 1000 succinate, antibody-conjugated PEG-ylated lipid, peptide-conjugated PEG-ylated lipid, DNA-conjugated PEG-ylated lipid, RNA-conjugated PEG-ylated lipid, biotin-modified PEG-ylated lipid, maleimide-modified PEG-ylated lipid, amine-modified PEG-ylated lipid, and the combination thereof or derived polymers thereof.

6. The method as claimed in claim 1, wherein the one or more molecules capable of getting across a lipid membrane and decreasing van der Waals forces between lipids is selected from the group consisting of:
polyethylene glycol, peptide, albumin, amino acid, sugar alcohols, butane-1,3-diol, propane-1,2,3-triol, propane-1,2-diol, propane-1,3-diol, propan-1-ol, ethane-1,2-diol, ethanol, methanol, dimethyl sulfoxide, and the combination thereof.

7. The method as claimed in claim 1, wherein the aqueous solvent is water, or normal saline, or buffered saline.

8. The method as claimed in claim 1, wherein the step of emulsifying the lipid mixture with the aqueous solvent is realized by sonication, high-speed agitation, high-pressure homogenization, or membrane filtration.

9. The method as claimed in claim 1, wherein the predetermined gas is selected from the group consisting of:
halo-substituted hydrocarbon (perfluorocarbon), inert gas, Sulfur hexafluoride, nitrogen, oxygen, and air, or a combination thereof.

10. The method as claimed in claim 1, wherein the step of agitating in the mechanical manner is realized by sonication, manual shaking, high-speed mechanical agitation, microfluidic device/T-focusing, or co-axial electrohydrodynamic atomization micro-bubbling.

11. The method of claim 3, wherein the first lipid is selected from the group consisting of 1,2-dipalmitoyl-sn-glycero-3-phosphocholine, 1,2-dipalmitoyl-sn-glycero-3-phosphate, 1,2-dipalmitoyl-sn-glycero-3-phosphserine, 1,2-dipalmitoyl-sn-glycero-3-phospho-(1'-rac-glycerol), 1,2-dipalmitoyl-sn-glycero-3-phosphoethanolamine, 1,2-distearoyl-sn-glycero-3-phosphocholine, 1,2-distearoyl-sn-glycero-3-phospho-(1'-rac-glycerol), 1,2-distearoyl-sn-glycero-3-phosphoethanolamine, 1,2-distearoyl-sn-glycero-3-phosphate, 1,2- distearoyl-sn-glycero-3-phosphserine, and 1,2-distearoyl-sn-glycero-3-phospho-(1'-rac-glycerol).

12. The method of claim 11, wherein the first lipid is selected from the group consisting of 1,2-dipalmitoyl-sn-glycero-3-phosphocholine, 1,2-distearoyl-sn-glycero-3-phosphocholine, and 1,2-distearoyl-sn-glycero-3-phospho-(1'-rac-glycerol).

13. The method of claim 5, wherein the second lipid is selected from the group consisting of: 1,2-dipalmitoyl-sn-glycero-3-phosphoethanolamine-N-[methoxy(polyethylene glycol)-2000], 1,2-dipalmitoyl-sn-glycero-3-phosphoethanolamine-N-[methoxy(polyethylene glycol)-3000], 1,2-dipalmitoyl-sn-glycero-3-phosphoethanolamine-N-[methoxy(polyethylene glycol)-5000], 1,2-distearoyl-sn-glycero-3-phosphoethanolamine-N-[methoxy(polyethylene glycol)-2000], 1,2-distearoyl-sn-glycero-3-phosphoethanolamine-N-[methoxy(polyethylene glycol)-3000], 1,2-distearoyl-sn-glycero-3-phosphoethanolamine-N-[methoxy(polyethylene glycol)-5000], polyoxyethylene stearates, and polyethylene glycol stearates.

14. The method of claim 13, wherein the second lipid is 1,2-dipalmitoyl-sn-glycero-3-phosphoethanolamine-N-[methoxy(polyethylene glycol)-2000], polyoxyethylene stearates, or polyethylene glycol stearates.

* * * * *